(12) United States Patent
Rickert et al.

(10) Patent No.: US 8,509,904 B2
(45) Date of Patent: Aug. 13, 2013

(54) BCI APPARATUS FOR STROKE REHABILITATION

(75) Inventors: Jörn Rickert, Freiburg (DE); Jörg Fischer, Reute (DE)

(73) Assignee: Cortec GmbH, Freiburg (DE)

( * ) Notice: Subject to any disclaimer, the term of this patent is extended or adjusted under 35 U.S.C. 154(b) by 129 days.

(21) Appl. No.: 13/112,594

(22) Filed: May 20, 2011

(65) Prior Publication Data

US 2011/0295338 A1  Dec. 1, 2011

(30) Foreign Application Priority Data

May 27, 2010 (EP) .................................... 10164126

(51) Int. Cl.
*A61N 1/36* (2006.01)
(52) U.S. Cl.
USPC .......................................................... 607/45
(58) Field of Classification Search
USPC .................................. 607/45, 47, 48; 600/544
See application file for complete search history.

(56) References Cited

U.S. PATENT DOCUMENTS

| | | | |
|---|---|---|---|
| 7,120,486 B2 | 10/2006 | Leuthardt et al. | |
| 7,826,894 B2 * | 11/2010 | Musallam et al. | 600/544 |
| 2006/0149338 A1 * | 7/2006 | Flaherty et al. | 607/49 |
| 2007/0032738 A1 | 2/2007 | Flaherty et al. | |
| 2009/0306531 A1 * | 12/2009 | Leuthardt et al. | 600/544 |

OTHER PUBLICATIONS

Meng, Fei et al., "BCI-FES training system design and implementation for rehabilitation of stroke patients", 2008 International Joint Conference on Neural Networks (IJCNN 2008), 2008, pp. 1403-1406.
Daly, Janis J. et al., "Brain-Computer interfaces in neurological rehabilitation", Lancet Neural, 2008, pp. 1032-1043, vol. 7.
Ball, Tonio et al., "Differential representation of arm movement direction in relation to cortical anatomy and function", Journal of Neural Engineering, 2009, pp. 1-16, vol. 6, IOP Publishing.

(Continued)

*Primary Examiner* — Carl H Layno
*Assistant Examiner* — Paula J Stice
(74) *Attorney, Agent, or Firm* — Nath, Goldberg & Meyer; Jerald L. Meyer; Stanley N. Protigal

(57) ABSTRACT

A BCI apparatus (10) for supporting the rehabilitation of stroke patients (12) with motor impairments is provided, comprising a probe (18) for recording a neuronal activity signal, an evaluation unit (24) for analysis of the activity signal, and an effector (18, 22, 26, 28) which is controlled by the evaluation unit (24) in dependence of a detected motion, wherein a session control unit (24) is configured to output a request to the patient (12) to generate a desired activity pattern, to at the same time record the activity using the probe (18), and to give the patient (12) a feedback via the effector whenever the desired activity pattern is identified by the evaluation unit (24). The request includes an instruction to imagine a specific movement or to try to execute the specific movement, wherein the probe (18) is an ECoG electrode with at least twenty individual electrodes (30), and wherein the evaluation unit (24) is configured to provide a plurality of frequency channels for the identification of the desired activity pattern and to evaluate the activity signal based on at least one of the amplitude and the phase in the frequency channels.

20 Claims, 3 Drawing Sheets

(56) References Cited

OTHER PUBLICATIONS

Wang, Chuanchu et al., "A Feasibility Study of Non-Invasive Motor-Imagery BCI-based Robotic Rehabilitation for Stroke Patients", Proceedings of the 4th International IEEE EMBS Conference on Neural Engineering, Antalya, Turkey, Apr. 29-May 2, 2009, pp. 271-274.

Buch, Ethan et al., "Think to Move: a Neuromagnetic Brain-Computer Interface (BCI) System for Chronic Stroke", Stroke, 2008, pp. 910-917, vol. 39.

Ward, Nick S., "The Neural Substrates of Motor Recovery After Focal Damage to the Central Nervous System", Arch Phys Med Rehabil, 2006, pp. S30-S35, vol. 87, Suppl. 2.

Extended European Search Report issued on Nov. 19, 2010, in corresponding European Application No. 10164126.4.

* cited by examiner

BCI APPARATUS FOR STROKE REHABILITATION

BACKGROUND

1. Field

The present disclosure relates to a brain-computer interface apparatus for supporting the rehabilitation of stroke patients with a probe for recording a neuronal activity signal, an evaluation unit for analysis of the activity signal, and an effector.

2. Background

In recent years, interest in BCI systems (brain-computer interface) has strongly increased. Generally, this refers to systems that enable the direct control of technical devices by analysis of the brain activity, or that conversely effect a stimulation of the brain. The term is often used in a somewhat narrower sense for medical motor applications, where at least a part of the autonomy lost by a health impairment is restored to patients by prostheses or a cursor control.

Various methods are known to measure the neuronal activity of a patient. There is an inverse interdependence of the resolution of the recorded activity information and the degree of having to invasively intervene with the body. At one end of the scale are EEG (electroencephalography) or MEG (magnetoencephalography) that use only external electrodes, yet also allow for but a relatively coarse spatial resolution. At the other end of the scale action potentials of individual cells (SUA, single unit activity) or local field potentials (LFP) may be recorded with electrodes penetrating the brain tissue. This allows for a high spatial resolution, but causes a virtually permanent open wound with the corresponding symptoms and risks of infection. Moreover, it is difficult to achieve a recording with long term stability. An intermediate solution is offered by ECoG electrodes (electrocorticography) that are arranged directly on the surface of the brain below the skull. They are long-time compatible and provide significantly improved spatially resolved neuronal activity information as compared to EEG or MEG. Such a BCI is presented in U.S. Pat. No. 7,120,486 B2. The paper of Tonio Ball and others, "Differential representation of arm movement direction in relation to cortical anatomy and function," J. Neural Eng. 2009:6 No. 016 006 studies which frequency ranges of an ECoG probe show a highly movement specific decoding power.

The vast majority of the previously discussed medical applications are intended for patients with motor impairments where an organic healing is no longer possible, although the cortex, or at least the motor cortex as the area that is essential for the control of voluntary movements, is at least partially intact, whereas the nerve connections to the musculature are interrupted. The BCI system is therefore to be regarded as a pure neural prosthesis that replaces a natural function of the body without healing it.

As long as a residual mobility is preserved, the healing can be supported by specific physiotherapy. As soon as a body part is completely paralyzed, the only attempt left for the traditional medicine is to passively and externally move the affected body part. But this is usually not sufficient to initiate a neuronal reorganization in the brain areas affected by the stroke, which might improve the motor impairment.

Ethan Buch and others in "Think to Move: a Neuromagnetic Brain-Computer Interface (BCI) System for Chronic Stroke", Stroke 2008:39, pages 910-917, have taught stroke patients to open or close a paralyzed hand with the aid of an orthosis (orthopedic prosthesis). An orthosis supports a movement of a body part, but does not replace the body part. For the control of the orthosis, patients were to achieve, by relaxing, a synchronization or desynchronization, i.e. a strengthening or weakening, of a neuronal activity analyzed by MEG, which is then translated into the corresponding opening state of the orthosis. Although the control could be successfully learned, no improvement of the motor impairment was achieved. A further disadvantage of this method is that the patients had to learn generation of artificial brain activity and not necessarily brain activity specific for the movement of the paralyzed body part. In this case, mu activity in the band of 8-12 Hz was evaluated, that can like beta activity in the band of 18-26 Hz be primarily detected above the somatosensoy an motor cortices. Movement or movement preparation are often associated with a reduction of mu and beta rhythms, while after a movement or during relaxation a temporary strengthening of rhythms usually takes place. Subjects can learn to purposefully influence these activities, but this takes a lot of concentration and is also very time consuming Moreover, mu and beta activity only indicates movement as such, but is not suitable to decode or predict specific movements or movement intentions.

Janis Daly and Jonathan Wolpaw in "Brain-computer interfaces in neurological rehabilitation," Lancet Neurol. 2008:7, pages 1032-1043, discuss the idea to directly train specific activity patterns without use of an orthosis. However, the paper is silent on the issue of what activity patterns these might be and how they could be identified from the recorded neuronal activity.

Another idea from Nick Ward, "The Neural Substrates of Motor Recovery After Focal Damage to the Central Nervous System", Arch Phys. Med. Rehabil. 2006:87 Suppl 2, Pages S30-S35 is to electrically stimulate the motor cortex. This is not related to an identification of specific neuronal activity of the patient, though, but only with traditional physiotherapy. A BCI system for stroke rehabilitation is thus not addressed in any way.

It is known that electrical stimulation can generally promote healing of damaged brain tissue. However, there is no evidence that a treatment of motor impairments following a stroke by electrical stimulation alone shows any success. This isolated stimulation was, for example, tried out in a study of Northstar Neuroscience Inc. and did not lead to the desired results (see, for example, at http://www.reuters.com/article/idUSWNAS705820080122).

SUMMARY

It is therefore desired to support the stroke rehabilitation with a BCI and to therewith open up new paths to an improved recovery.

This object is satisfied by a BCI apparatus for supporting the rehabilitation of stroke patients with motor impairments and having a probe for recording a neuronal activity signal, an evaluation unit for analysis of the activity signal, and an effector which is controlled by the evaluation unit in dependence of a detected motion, in which a session control unit is configured to output a request to the patient to generate a desired activity pattern, to at the same time record the activity signal using the probe, and to give the patient feedback via the effector whenever the desired activity pattern is identified by the evaluation unit, characterized in that the request includes an instruction to imagine a specific movement or to try to execute the specific movement, in that the probe is an ECoG electrode with at least twenty individual electrodes, and in that the evaluation unit is configured to provide a plurality of frequency channels for the identification of the desired activity pattern and to evaluate the activity signal based on at least one of the amplitude and the phase in the frequency channels. The disclosed technology starts from the basic idea to specifically train those activity patterns that are associated with movements of a body part that is impaired or paralyzed by a stroke. With that, the reorganization of the brain is supported by specifically training neuronal activity facilitating a recovery. The BCI apparatus gives a feedback quickly or even in real time whether or not such beneficial neuronal activity could be detected during a training run.

BRIEF DESCRIPTION OF THE DRAWINGS

The disclosed techniques will be explained in the following also with respect to additional features and advantages with reference to exemplary embodiments and the accompanying drawing. The Figures of the drawing show in.

DETAILED DESCRIPTION

Overview

Figure 1:
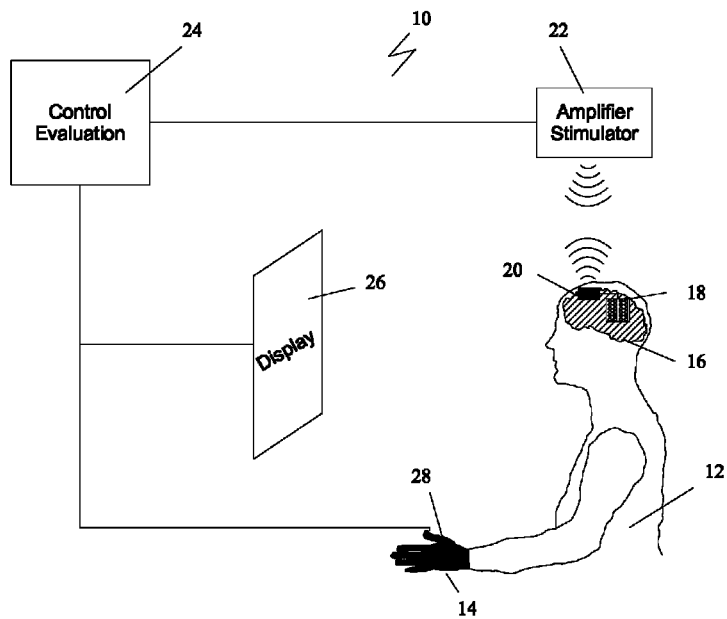
FIG. 1 an overview of a BCI apparatus for stroke rehabilitation.

In contrast to that, with conventional BCI systems used as a pure neural prosthesis it is not attempted to generate a specific neuronal activity, but it is merely observed in the attempt to derive a movement intention. Therefore, in the prior art, movements are at most instructed during a training in order for the BCI system to learn correlations between neuronal activity and movement. In the course of such training the patient receives no feedback; rather, the BCI apparatus accepts the neuronal activities as a reference without evaluating them.

Thus, while the disclosed technique distinguishes between desired neuronal activity presumed to support the rehabilitation and other neuronal activity, no such distinction exists in conventional BCI systems. As far as in some known EEG-based BCI systems a specific activity pattern is to be learned, like reinforcement of mu rhythms, this is artificial and linked to the movement solely because of the artificial training. Such training leads, as the paper of Ethan Buch and others cited above shows, to no reorganization and improvement of motor impairments. According to the present disclosure, specific movements are preset and decoded, for example a body part, a movement direction, a movement speed, or the like. That is not possible for the signals used in the prior art that are only correlated with movement as such, like mu or beta rhythms.

The concept of motion is used in a wide enough sense to encompass generation of speech to begin with. As a more specific option movements in a narrower sense are advantageously supported by the disclosed technique, for example movement of an arm, a hand, a leg, or another body part.

The disclosed techniques have the advantage that stroke patients can take part in effective rehabilitation measures who previously have been excluded therefrom. This results in an improved recovery of mobility with the associated benefit on independence and quality of life.

According to the present disclosure, the effector may be controlled in dependence of the movement. The success feedback generated in this manner is advantageously linked to the specific movement to be imagined or executed, for example in that an orthosis executes the real movement or an avatar a virtual movement. An abstract feedback is also conceivable, like a display that shows the degree of correlation between the measured activity signal and the desired activity pattern.

By recording with a plurality of individual electrodes, for example at least twenty, at least one hundred or even at least four hundred individual electrodes, a fine spatial resolution of the measured activity signal is achieved. With ECoG probes even finger movements can be detected, more so if they have a high resolution due to a high number of individual electrodes. The ECoG electrode may be implanted both epidurally and subdurally.

The desired activity pattern is identified by an amplitude and/or a phase information in a plurality of frequency channels, i.e. at least two frequency channels. The frequency channels are generally determined by Fourier transform (such as FFT, Fast Fourier Transform). Since not the entire spectrum has to be resolved, simplified estimators are used. In order to evaluate the signal in the frequency channels formed in this manner, it is averaged over equal or different time slots.

The effector preferably comprises an orthosis which is designed for the support or execution of the specific movement on a body part. Through the link between the neuronal activity during the movement imagination or the attempt of the movement execution and an actual, externally performed movement the brain is particularly effectively motivated to reproduce the link also by reorganization and thus to reduce the motor impairment. Alternatively, the effector comprises a display device for displaying the successful identification of the specific movement, in particular as an image sequence of the specific movement. There is not always an appropriate orthosis available, so that the visualization of the movement still comes closest to the actual movement.

The effector, be it an orthosis or a display device or other means, which gives the patient feedback about the degree of success of control, responds in a preferred embodiment at the beginning of the rehabilitation, when the brain is still damaged more severely, to a roughly similar brain activity with a corresponding roughly similar movement. For example, a correlation coefficient is determined that evaluates the degree to which the desired activity pattern is identifiable in the activity signal. The effector is controlled with a corresponding accuracy. For a better motivation the movement carried out by the effector is always a little more precise and better than the neuronal activity, there is, hence, an advance of the orthosis. Because at any one time one particular movement is practiced, the movement to be carried out is known to the BCI apparatus with the maximum accuracy of the system. For example, at the beginning of the rehabilitation only a rudimentary movement is executed based on a deviation of the neuronal activity from a background noise, wherein the magnitude of the movement is adapted to a magnitude of the deviation. Later, when the activity becomes more differentiated and perhaps a partial movement has already been regenerated, the effector also responds to more specific activations with more specific movements that more and more correspond to the full, correct movement.

The effector preferably includes a stimulator for muscle or brain tissue, in particular for a stimulation with the desired activity pattern. Stimulation of the muscle tissue in the best case leads to prompting an independent movement of the paralyzed body part by artificial signals. A sensory feedback from the paralyzed body part may also be helpful for the reorganization. Stimulation of the brain tissue is preferably carried out in the vicinity of the lesion to stimulate activity there. If the body part to be rehabilitated lacks feeling, a stimulation can additionally or alternatively be carried out with an additional or the same ECoG electrode that is placed on the corresponding somatosensoy brain areas. This supports the regeneration especially in case that these somatosensoy brain areas are also affected by the stroke. By presenting the desired activity pattern via stimulation, the brain learns to again generate these activity patterns itself Alternatively, however, an inhibitory stimulation is also conceivable, for example of a contralateral area, to prevent other brain areas to adversely influence the desired activity pattern.

In another configuration, the movement of the effector is combined with a stimulation. In particular, the stimulation is coupled to the movement of the orthosis. As the prior art discussed above shows, frequently neither with stimulation alone nor with an orthosis movement alone a sufficient rehabilitation can be achieved. By the combination a chain of associations between movement imagination or movement control, an actual movement success achieved by the effector, and a matching stimulation of the damaged brain tissue is created that leads, as a whole, to a particularly successful reorganization.

Preferably, different movements produce different movement specific stimulation patterns that stimulate the places on the damaged tissue around the movement-inducing electrode. One example of such a stimulation pattern is the desired activity pattern or an activity pattern derived therefrom. One therefore tries, as far as this is possible with an ECoG electrode lying on the surface or being inserted into a sulcus, to directly impress the trained activity patterns on the damaged brain area and its surroundings.

The evaluation unit is preferably configured to provide frequency channels only for a number of selected individual electrodes, wherein the same frequency channels are provided for all selected individual electrodes or different frequency channels are provided for different ones of the selected individual electrodes. This will only include activity signals which are related to the movement to be imagined or to be executed. The evaluation causes less effort and is at the same time more accurate since the movement related activity is less diluted. In the simplest case electrodes are excluded that provide no signal at all or a uniform noise signal at all times. More specific criteria are used in a training before the actual rehabilitation session. For the electrodes selected in this manner either the same frequency channels are provided, or one or more frequency channels are assigned to some of the selected electrodes or each selected electrode, respectively. All in all, a parameter space is formed that is built up by the sum of the frequency channels assigned to the respective selected electrodes. By evaluating amplitude and phase or correlations between these previously mentioned parameters, the number of parameters may yet multiply accordingly. In adjusting the presence of the desired activity pattern to the patient instead of simply search across all electrodes in the same frequency range using the same criteria, the evaluation effort is reduced, while at the same time the decoding power and with it the accuracy of the identification of desired activity increases. Here, decoding power is meant to be a measure of how specific and reliable a movement selective neuronal activity is identified.

The evaluation unit is preferably configured to select the individual electrodes and/or the frequency channels for the individual electrodes on the criterion that the activity signal differs from a basic activity in a movement selective way. Deviations upwards or downwards are detected with threshold values corresponding to a significance threshold. It is conceivable to do without a significance threshold in order not to overstress the requirements and to also reinforce a random deviation by positive feedback.

The evaluation unit is preferably configured to provide a low frequency channel with a lower limit of 0 Hz to 2 Hz and an upper limit of 4 Hz to 10 Hz and/or a high frequency channel with a lower limit of 50 Hz to 70 Hz and an upper limit of 100 Hz to 120 Hz or more. It has been shown that movement selective activity is particularly well identifiable in these frequency channels of an ECoG signal. In the excluded band between about 10 Hz and about 50 Hz, however, which means also in the conventionally used mu and beta bands, the decoding power is lower. The excluded band can be used as a supportive pure movement detector, i.e. to independently of a specific movement detect that a movement is generally intended or executed. An information significant for the specific movement can only be extracted from the excluded bands to a very limited degree or not at all, so that other frequencies are used for the decoding of the specific movement.

One can push the lower limit of the high frequency channel further down than only to 50 Hz, but this does not lead to substantially improved results. The upper limit, however, may also be higher than 120 Hz.

The evaluation unit is preferably configured to split the high frequency channel into a lower high frequency channel with a lower limit of 50 Hz to 60 Hz and an upper limit of 90 Hz to 100 Hz and an upper high frequency channel with a lower limit of at least 100 Hz and an upper limit of at least 20 Hz above the lower limit. Thus, a total of three frequency channels with a greater parameter space is available. Each frequency band with the exception of the low frequency band should have a width of at least 10 Hz for a sufficient decoding power.

The request for the specific movement preferably includes an indication of a direction. In some cases, the request consist of only the indication of a direction. This may be divided into sectors, for example into the four main directions of an orthogonal coordinate system, or the sectors of a clock, and can be detected from the neuronal activity signal quite reliably. The request in particular relates to an arm movement or a hand movement. The neuronal activity during these movements is relatively well understood, and the regained use of the hand really helps a patient.

The evaluation unit is preferably designed for a real time evaluation. In contrast to conventional neural prostheses a real time evaluation is not inevitable, so that short delays for example for a more reliable identification of the desired activity pattern can be accepted. The faster the success feedback comes, however, the more satisfying and effective is the rehabilitation session for the patient.

Several approaches for the desired activity pattern are provided. They may be applied in parallel or alternately, but also depend on the degree of impairment of the cortex of the patient. In case the cortex responsible for the movement to be rehabilitated is still active enough to generate differentiated activity patterns, these may be taught in an initial training and then be selectively practiced and improved. Otherwise, other references have to be used, some of which are discussed below.

In that context, the evaluation unit is preferably configured to accept any activity signal as the desired activity pattern that differs from a basic activity without the specific movement. Generally, the desired activity pattern should be the one that optimally supports the reorganization. This is, for example, an activity that is close to the one which the patient used to move the paralyzed body part prior to the stroke. However, this activity pattern is in the majority of cases unknown. Additionally, the brain is no longer able to reproduce it due to the lesion. Hence, the desired activity pattern is in fact the a priori unknown activity pattern that will be reached after a successful rehabilitation. As a first step in this direction it is monitored if any significant deviation of a basic activity and an activity during the movement imagination or the attempted movement can be detected at all. A special case are individual electrode above the lesion or in the vicinity of the lesion that were previously inactive. Any activity occurring there is a sign of incipient reorganization, which is supported by the BCI apparatus by the success feedback. To that end, for example, a standard movement or the movement currently to be practiced according to the request is executed by the effector. In this way, it can still be proceeded even with relatively severe damage of the participating brain tissue and little knowledge about the movement specific activity of the patient.

The evaluation unit is preferably configured to accept an activity signal as the desired activity pattern that does not differ by more than an upper limit from an activity signal that was trained in the contralateral brain region during the specific movement of the contralateral body part. This is a replacement for the unavailable activity signal of the brain tissue affected by the stroke that originates from the same patient with an analogous movement and therefore has some significant similarities. For example, the frequency ranges in which movement specific activity shows are often the same in different areas for one and the same person. In order to at least partially avoid the invasive surgery on the per se healthy brain hemisphere, a short-time implant can be implanted rather than a permanent implant for recording the neuronal activity. Furthermore, it is preferably only implanted there epidurally and not subdurally, or even only an EEG signal is used. Instead of a signal of the patient's own healthy brain hemisphere a generic signal of a healthy person may also be used as a reference.

A complete healing of the damaged area is to be expected in the fewest cases. It is therefore unrealistic to assume that by rehabilitation neuronal movement activity can be trained that is identical to a healthy motor cortex. For that reason, in a particularly preferred embodiment a reference signal form a healthy brain area of the patient or a generic reference signal derived from healthy individuals is only initially used for the rehabilitation. Once it was possible to even recover a minimal movement ability of the paralyzed body part, those activity patterns are practiced and stimulated in the further rehabilitation that generate these movement in order to reinforce and differentiate them. Thus no allegedly correct activity pattern is forced on the damaged brain area, which might not even be possible to generate due to the damage, but instead a natural restructuring and reorganization of the brain is supported for a facilitation of new controls of the paralyzed body part.

The evaluation unit is preferably configured to accept an activity signal as the desired activity pattern which results in a modified activity signal in individual electrodes in the vicinity of the selected electrodes. The electrodes were selected because they record movement specific activity. If their neighbors now also show a modified activity, this is a sign of an incipient reorganization in response to the movement. The BCI apparatus supports this reorganization by a success feedback.

The evaluation unit is preferably configured to accept an activity signal that was previously recorded as the desired activity pattern. Possibly the earlier activity of the brain area affected by the lesion from a time previous to the lesion is known. This recording can for example be done prior to a new stroke in multiple strokes or during a preventive medical checkup. Alternatively, it is an activity signal established during a training or an activity signal that was recorded during a partial success. Such a partial success can be a partial movement, or a tremor of the paralyzed body part, or some action potentials in the paralyzed body part. Therewith, partial successes are secured and reinforced.

The session control unit is preferably configured for an initial or cyclic training mode during which the frequency channels, in particular also the selected electrodes and associated frequency channels, as well as criteria for movement selective activity signals in the frequency channels, in particular of the selected electrodes, are determined. Thus, the BCI apparatus is adapted to a patient in order to individually support his rehabilitation.

The BCI apparatus advantageously comprises an amplification and stimulator unit with a fastening device on the body of the patient and with a connection to a computer system with the evaluation unit which is in particular connected to the effector that is designed as the display device or orthosis, wherein the probe is configured as an implant for the permanent arrangement below the skull and includes a wireless interface for the connection to a wireless interface of the amplification and stimulator unit. Because of the wireless connection the skull and scalp can heal completely after the implantation of the ECoG probe. The amplification and stimulator unit is preferably external and is located near the patient, for example in a shoulder bag or a headdress, so that the wireless transmission path remains short and free of interference. It can be relatively small, since the required computing power is provided in the external computer system. The wireless interface supplies current and voltage, respectively, to the implant for example by induction, so that no exchange of an energy source is required.

EXAMPLES

FIG. 1 shows an overview of a BCI system 10 which supports the rehabilitation of a patient 12 affected by a stroke. Because of the stroke the patient 12 has motor impairments in a body part which in the illustrated example is the left hand 14. Likewise also the arm, a leg or another arbitrary body part can be affected.

On the brain 16 of the patient, an ECoG probe 18 for the recording of the neuronal activity is implanted. The ECoG probe 18 is placed onto the surface of the brain tissue within the skull. The location of the implantation is determined by general anatomic knowledge or by preoperative diagnosis. Preferably the ECoG probe 18 is placed above an area of the motor cortex and/or the somatosensory cortex that is responsible for the paralyzed or impaired body part 14 or its vicinity.

The ECoG probe 18 is connected to a wireless interface 20 that is also implanted within the skull. It is in principle also possible to lay a connection line through the skull, but this constrains the patient 12 considerably more. The wireless interface is preferably bidirectional an can include a micro controller for the preprocessing or circuit elements for the preamplification of the signals from and to the ECoG probe 18.

Near to the patient 12, for example in a headdress, at the patient's bed or in a shoulder bag, there is an amplification and stimulator unit 22 that includes a counterpart of the wireless interface 20 and can thus exchange information and commands with the implanted ECoG probe 18 or the micro controller of the wireless interface 20. Via the wireless interface 20 the implants 18, 20 are also supplied with current and voltage, respectively. The amplification and stimulator unit 22 can also be implemented on a mobile device, like a mobile phone or a PDA. In one embodiment, data traffic on the air interface 20, 22 is encrypted or secured by an authentication, respectively, to exclude accidental or intentional misuse.

An evaluation and control unit 24 is connected to the amplification and stimulator unit 22. This is, for example, a desktop computer, a notebook or the like. In principle it is possible to integrate amplification and stimulator unit 22 and evaluation and control unit 24 in one device. However, since a relatively high computing capacity is required for the analysis of the neuronal activity in the evaluation and control unit 24, this may limit the mobility.

The evaluation and control unit 24 in turn is connected with a display device 26 and an orthosis 28 that is represented as a black coloring of the hand 14. The orthosis is able to execute or support movement of the paralyzed or impaired hand, for example an opening and closing movement.

Figure 2:
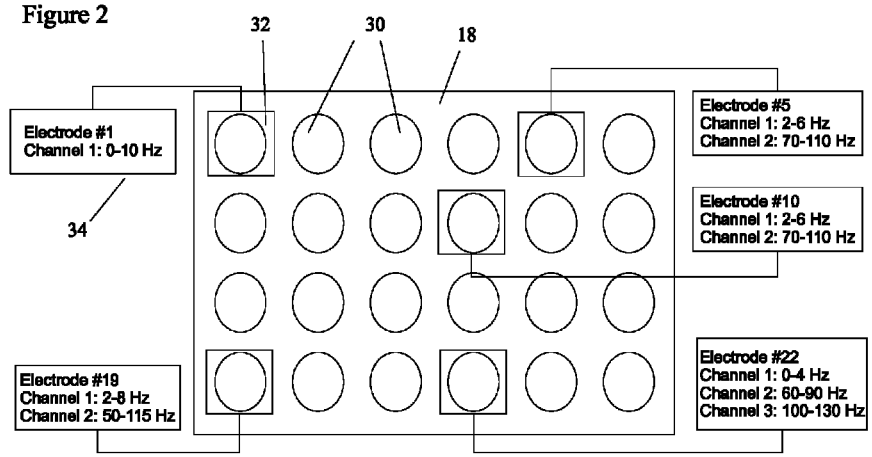
FIG. 2 a plan view onto an ECoG electrode illustrating selected individual electrodes and associated frequency channels.

FIG. 2 shows an enlarged plain view onto the ECoG probe 18 comprising a support of a biocompatible material and a plurality of individual electrodes 30. The layout of the individual electrodes may vary, even by a personal adjustment to the patient 12, and a different number of individual electrodes 30 from eight to thirty-two up to several hundred individual electrodes 30 is possible. In the majority of cases individual electrodes 30 are provided on one side of the support only. But there is also the possibility to arrange individual electrodes on both sides of the support and to implant the ECoG probe 18 in a sulcus (furrow) of the brain 30. This enables access to additional brain areas, as described in the patent DE 10 2006 008 501 B3.

The individual electrodes 30 are both able to measure activity of the brain 16 and to output a corresponding activity signal via the wireless interface 20 and to stimulate the subjacent area of the brain 16 with a current or a voltage.

Not all individual electrodes 30 contribute to the measured activity signal or the stimulation. During a training that is discussed below with reference to FIG. 4, or by the attending physician, individual electrodes 30 are selected that are especially correlated with movements, sensory stimuli or movement imaginations of the paralyzed hand. Examples of selected electrodes 32 are marked by a rectangle in FIG. 2. By the selection of individual electrodes 32, on the one hand, a more specific measurement or stimulation is achieved. On the other hand, also less data traffic is generated at the wireless interface 20, if the individual electrodes 30 that are not selected are already silenced by the micro controller of the implant 18, 20.

Individual electrodes 32 are, however, not only selected, but also specific signal properties are assigned to these individual electrodes 32. To that end, frequency channels are provided and the amplitude or phase in these frequency channels is evaluated. FIG. 2 shows some frequency channels 34 by way of example that are individually assigned to the individual electrodes 32. Alternatively it is possible to assign uniform frequency channels to all selected individual electrodes 32.

Figure 3:
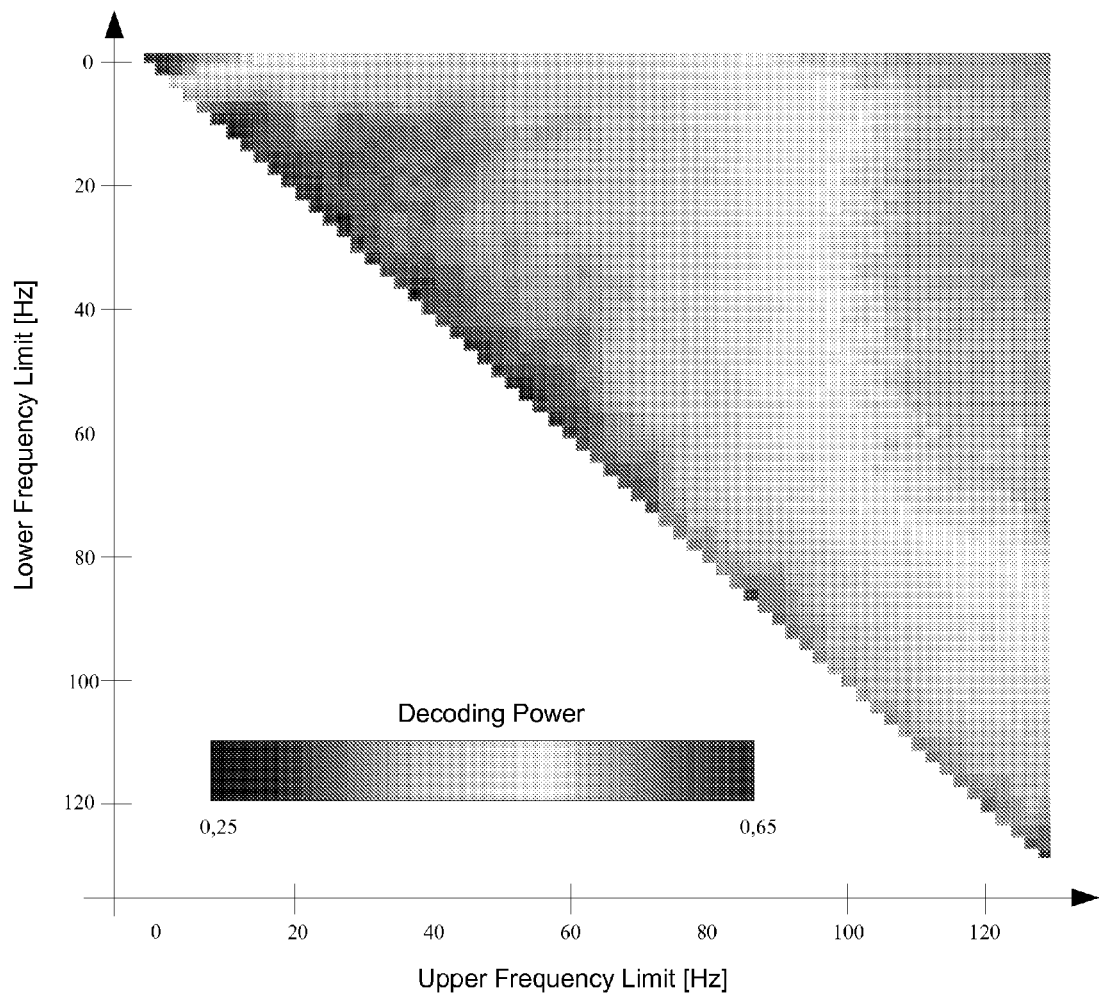
FIG. 3 a diagram in which the decoding power in frequency bands between a lower limit plotted on the Y-axis and an upper limit plotted on the X-axis is represented.

FIG. 3 shows a representation of the decoding power in dependence of the lower and upper limit of a frequency channel adapted from the paper of Tonio Ball and others cited above. From this, frequency intervals can be determined in which the activity varies with movement imagination or movement of the hand 14 in a particularly specific way. For example, it can be read from FIG. 3 that frequency channels with a lower limit at about 10 Hz and an upper limit at about 50 Hz have a very low decoding power only. Such a frequency channel is therefore not a favorable choice for detecting a movement or a movement intention. In contrast, there are other ranges, for example a low frequency channel between about 0 Hz and 8-10 Hz or a high frequency channel between about 60 Hz and 100 Hz or a channel about 100 Hz in which the decoding power is high according to the color coding, i.e. exceeds a threshold. With an appropriate choice of these parameters, the evaluation of the neuronal activity is considerably improved.

Figure 4:
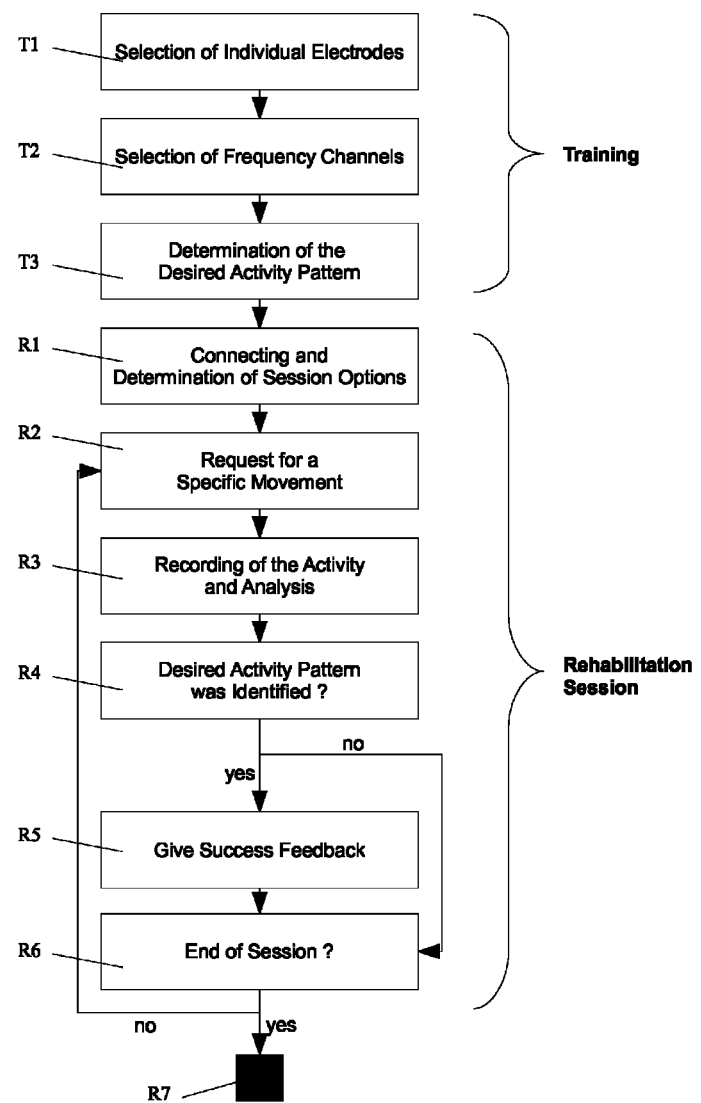
FIG. 4 a flow chart of a training and a rehabilitation session.

Use and functionality of the BCI system 10 by the patient 12 will now be further explained with reference to the flow chart of FIG. 4. Here, a distinction is made between a training phase and the actual rehabilitation session. The training is initially carried out under guidance of the physician and is subsequently repeated after a certain time or on demand. However, a training is not imperative, but it can also be worked with generic parameters.

In a first training step T1 the selected individual electrodes 32 are determined. Among exemplary selection criteria are that an individual electrode provides any signal in the first place, that it differs from pure noise, that it respectively appears during a movement or a movement attempt, a movement imagination or a movement observation or, in the optimal case, that it specifically indicates certain movements or movement imaginations. During the training or upon completion thereof, more time is available for evaluations than within a rehabilitation session. It is therefore possible, for example, to simulate the movement prediction in the evaluation and control unit 24 experimentally for different groups of selected individual electrodes 32 and to subsequently use the one selection that provides the best results.

Then, in a second training step T2, suitable frequency channels are assigned to the selected individual electrodes 32. This selection can be made according to general criteria, as illustrated in FIG. 3, but can also be individually further adapted to the patient 12. Again, as with the selection of the individual electrodes 32, enough computing time is available for the evaluation and control unit 24 to find a set of frequency channels by complex or time-consuming methods or simulations that individually provide the best results for the patient 12. The computing power of the evaluation and control unit 24 can in principle be upgraded to any level by additional hardware or a network connection to additional computers.

In a third training step T3, a desired activity pattern is determined which is to be learned or reinforced by the patient 12 by the subsequent rehabilitation session in order to stimulate or accelerate a reorganization for the recovery of mobility. Hence, this is a static or dynamic pattern in the parameter space that is formed by amplitudes and/or phases in the frequency channels assigned to the selected individual electrodes 32, that are for example averaged over a time interval, respectively. In the simplest case the pattern is identified merely by a threshold evaluation, i.e. by smaller or higher values in the respective parameters than in a resting state. Correlations of these variables over different individual electrodes 32, frequency channels, or time intervals can also be part of the parameter space.

Different approaches are conceivable at a time to find desired activity patterns supporting the rehabilitation, wherein these approaches can also be used in combination or alternately.

In one approach, the activity of the corresponding contralateral brain hemisphere at the corresponding movement is determined In this example, this would be a movement of the healthy right hand. This provides indications of which frequency channels are suitable and of the characteristics of the signal course during a successful movement. The patient 12 subsequently is to learn to generate an activity pattern with the brain area affected by the stroke that is similar to the activity pattern of the opposite healthy brain area. In this case, alternatively to the steps T1 and T2 the activity of the healthy area can be measured and analyzed with an additional EEG system.

A very easy to use desired activity pattern is one which generates any arbitrary activity or modification of activity in the vicinity of the lesion at all. This activity pattern is also analyzed in the parameter space as discussed and is thus correlated with a movement or movement intention of the paralyzed hand 14. As the patient 12 cannot any more move the paralyzed hand 14 in everyday life, the brain lacks any stimulation for a reorganization without a rehabilitation session.

Ideally, the patient 12 shows some first rehabilitation successes. The associated modifications of the activity or an extrapolation thereof are then systematically conserved or reinforced during further rehabilitation sessions.

Once a desired activity pattern to be learned or improved by the rehabilitation session is determined, the training is complete. However, the choices made in the steps T1 to T3 can also be changed at a later time.

During a rehabilitation session following the training directly or later, the evaluation and control unit 24 is connected to the amplification and stimulator unit 22 in a first step R1, and both are activated. Via the wireless interface 20 the implant 18, 20 is also put into an operating state. Optionally, session parameters are set, like a specific patient 12 is selected, or a number of repetitions or a duration of the session is determined In a second step R2, the evaluation and control unit 24 requests the patient 12 via a display device 26 to imagine a specific movement of the paralyzed hand 14 or to try to execute this movement with the paralyzed hand 14. This is for example an opening or closing movement. The patient 12 therefore is not to generate any artificial brain activity, but only the activity that would be associated with a specific natural movement. The goal of the rehabilitation is to achieve a reorganization, therefore to take advantage of the remaining pathways, or to expand or repair them.

Starting with the request, the ECoG probe 18 in a third step R3 records the neuronal activity and sends the corresponding signals of the selected electrodes 32 via the wireless interface 20 to the amplification and stimulator unit 22. From there, the amplified signals are transferred to the evaluation and control unit 24 for analysis. The necessary transformations, averagings and correlations are performed in real time or near real time in order to be able to evaluate the parameters that were selected during the trainings The evaluation and control unit 24 in a fourth step R4 decides whether the neuronal activity of the patient corresponds to the desired activity pattern based on this analyzed activity data. If that is not the case, the current practice run was not successful. The patient 12 can optionally be given a short feedback message about this via the display device 26.

In case the desired activity pattern is identified, a success feedback is given in a fifth step R5. Again, several different variants are conceivable which can be used simultaneously or alternatively. A very simple success feedback is a message on the display device 26. This is somewhat more impressive if it is done in form of a graphical representation of the desired movement of an avatar.

A more natural feedback is the execution of the movement designated in the request by the ortheses 28. If for example the request was to open the hand 14, the orthosis 28 stretches out the fingers accordingly. By linking the movement imagination or the neuronal movement command with an activity pattern that has a relation to this movement, and by the subsequent execution, exactly the chain of events is created that is to be achieved to alleviate the motor impairment.

Furthermore, a stimulation of the brain 18 is possible as a success feedback. For this, the amplification and stimulator unit 22 sends a corresponding command to the wireless interface 20, so that the individual electrodes 32 of the ECoG probe 18 stimulate the subjacent brain tissue. As with the desired activity pattern, several approaches are also possible for the stimulation. For example, the tissue in the area of the lesion or its vicinity can be stimulated. Alternatively, an associated somatosensory area is stimulated, or the corresponding areas of the healthy right hand in the contralateral brain hemisphere. In particular it is attempted to reproduce and to thus further reinforce the desired activity pattern by stimulation. Since the ECoG electrode rests on the surface, this is only possible within limits. Deeper tissue layers are reached with by an ECoG electrode that is placed in a sulcus.

With the success feedback, the current practice run is completed. In a sixth step R6 it is checked whether also the end of the rehabilitation is reached. In dependence thereof the rehabilitation session is continued at the second step R2 or completed at a seventh step R7.

In the described manner one or more specific movements can be systematically practiced and recovered. For these movements connections of the cortex to the muscles are created or reinforced by a feedback via the orthosis 28 and preferably also at the same time a stimulation via the amplification and stimulator unit 22.

As soon as at least one movement has been rudimentary learned, it can be switched over into a free mode of the BCI system 10 instead of a systematic rehabilitation session with preset movements. Therein, the patient 12 himself decides about the movement he performs. The BCI system 10 identifies the movement, for example to support it with the orthosis 28 or a stimulation by means of the amplification and stimulator unit 22. If the patient 12 is able to generate movement specific neuronal activity from the beginning, it is also possible to immediately start the rehabilitation in this free mode. If at this time the orthosis 28 has an advance, i.e. supports the intended movement with more accuracy than the patient 12 himself could achieve, the patient 12 at once gains additional movement options, and ideally accepts the rehabilitation as a support for his daily life from the very beginning. This does not only increase the quality of life, but the rehabilitation is also more successful, because the patient uses the system to a greater extent on his own initiative.

The invention claimed is:

1. A BCI apparatus (10) configured to support rehabilitation of stroke patients with motor impairments, comprising:
   a probe (18) configured to record a neuronal activity signal,
   an evaluation unit (24) operably connected to the probe and configured to analyze the neuronal activity signal, and
   an effector (18, 22, 26, 28) operably connected to and controlled by the evaluation unit,
   wherein the effector is controlled by the evaluation unit in response to a detected motion-related activity pattern detected in the neuronal activity signal detected by the evaluation unit,
   wherein the effector is configured to provide feedback about a degree of success of control of a motion related activity pattern detected in the neuronal activity signal, and
   wherein the effector includes a stimulator for brain tissue, and
   wherein the evaluation unit is further configured to output a request to the patient; the request including instructions to imagine a specific movement or to try to execute the specific movement, and wherein the probe (18) is an ECoG electrode with at least twenty individual electrodes (30), and wherein the evaluation unit is configured to provide a plurality of frequency channels for identification of the desired activity pattern and to evaluate the activity signal based on at least one of an amplitude and a phase in the frequency channels.

2. The BCI apparatus (10) of claim 1, wherein the effector comprises an orthosis (28) which is designed for support or execution of the specific movement on a body part (14), or a display device (26) for displaying a successful identification of the specific movement.

3. The BCI apparatus of claim 2, wherein the successful identification of the specific movement is displayed as an image sequence of the specific movement.

4. The BCI apparatus of claim 1, wherein the effector further includes a stimulator (22, 18) for muscle tissue.

5. The BCI apparatus of claim 4, wherein the stimulator (22, 18) is configured for a stimulation with the desired activity pattern.

6. The BCI apparatus of claim 1, wherein the evaluation unit (24) is configured to provide frequency channels only for the selected individual electrodes (32), by providing the same frequency channels are provided for all of the selected individual electrodes (32) or by providing different frequency channels for different ones of the selected individual electrodes (32).

7. The BCI apparatus of claim 6, wherein the evaluation unit (24) is configured to select at least one of the individual electrodes (30) and the frequency channels for the individual electrodes (32) on a criterion that the activity signal differs from a basic activity in a movement selective way.

8. The BCI apparatus of claim 6, wherein the evaluation unit (24) is configured to accept the neuronal activity signal recorded from the probe (18) as the desired activity pattern when a neuronal activity signal recorded from individual electrodes (30) in a vicinity of the selected electrodes (32) is modified as compared to a neuronal activity signal recorded previously from the individual electrodes (30).

9. The BCI apparatus of claim 1, wherein the evaluation unit (24) is configured to provide at least one of a low frequency channel with a lower limit of 0 Hz to 2 Hz and an upper limit of 4 Hz to 10 Hz and a high frequency channel with a lower limit of 50 Hz to 70 Hz and an upper limit of 100 Hz to 120 Hz or more.

10. The BCI apparatus of claim 9, wherein the evaluation unit (24) is configured to split the high frequency channel into a lower high frequency channel with a lower limit of 50 Hz to 60 Hz and an upper limit of 90 Hz to 100 Hz, and an upper high frequency channel with a lower limit of at least 100 Hz and an upper limit of at least 20 Hz above its lower limit.

11. The BCI apparatus of claim 1, wherein the request for the specific movement includes an indication of a direction relating to an arm movement or a hand movement.

12. The BCI apparatus of claim 1, wherein the evaluation unit (24) is designed for a real time evaluation.

13. The BCI apparatus of claim 1, wherein the evaluation unit (24) is configured to accept the neuronal activity signal recorded from the probe (18) as the desired activity pattern differs from a basic neuronal activity signal recorded from the probe without the specific movement.

14. The BCI apparatus of claim 1, wherein the evaluation unit (24) is configured to accept the neuronal activity signal recorded from the probe (18) as the desired activity pattern in the case of the activity signal not differing by more than an upper limit from an activity signal that was trained in the contralateral brain region during the specific movement of the contralateral body part.

15. The BCI apparatus of claim 1, wherein the evaluation unit (24) is configured to accept a previously-recorded activity signal as the desired activity pattern.

16. The BCI apparatus of claim 1, wherein the session control unit (24) is configured for an initial or cyclic training mode during which the frequency channels as well as criteria for movement selective activity signals in the frequency channels are determined.

17. The BCI apparatus of claim 16, wherein the selected electrodes (32) and associated frequency channels and the criteria for motion selective activity signals in the frequency channels of the selected electrodes (32) are determined during the training mode.

18. The BCI apparatus of claim 1, comprising an amplification and stimulator unit (22) with a fastening device on the body of the patient and with a connection to a computer system (24) with the evaluation unit.

19. The BCI apparatus of claim 18, wherein the computer system (24) is connected with the effector that is designed as a display device (26) or as an orthosis.

20. The BCI apparatus of claim 18, wherein the probe (18) is configured as an implant for the permanent arrangement below the skull and includes a wireless interface (20) for the connection to a wireless interface of the amplification and stimulator unit (22).

* * * * *